US00PP17228P2

(12) United States Plant Patent
White

(10) Patent No.: US PP17,228 P2
(45) Date of Patent: Nov. 21, 2006

(54) ***EPIMEDIUM* PLANT NAMED 'PINK ELF'**

(50) Latin Name: ***Epimedium* sp.**
Varietal Denomination: PINK ELF

(76) Inventor: Anthony Robin White, Blackthorn Nursery Kilmeston Alresford, Hampshire SO24 0NL (GB)

( * ) Notice: Subject to any disclaimer, the term of this patent is extended or adjusted under 35 U.S.C. 154(b) by 2 days.

(21) Appl. No.: 11/190,358

(22) Filed: Jul. 26, 2005

(51) Int. Cl.
*A01H 5/00* (2006.01)

(52) U.S. Cl. ..... Plt./263
(58) Field of Classification Search ..... Plt./263
See application file for complete search history.

(56) References Cited

PUBLICATIONS

Harris et al. Plant Identification Terminology an Illustrated Glossary 2nd ed. 2001, p. 23.*

* cited by examiner

*Primary Examiner*—Anne Marie Grunberg
*Assistant Examiner*—June Hwu

(57) ABSTRACT

A new cultivar of *Epimedium* plant named 'PINK ELF' that is characterized by clumping habit, leaflets that are green and russet in color, and purple-pink spurred flowers that are held above two distinct layers of foliage. In combination these traits set 'PINK ELF' apart from all other existing varieties of *Epimedium* known to the inventor.

4 Drawing Sheets

Genus: *Epimedium. Species: sp.*
Denomination: 'PINK ELF'.

BACKGROUND OF THE INVENTION

The present invention relates to a new and distinct cultivar of *Epimedium*, or bishop's hat, grown for use as an ornamental for container, rock garden, or as a groundcover for the landscape. The new cultivar is referred to hereinafter by the cultivar name 'PINK ELF' and is known botanically as *Epimedium* sp. since the identity of its pollen parent cannot be known with certainty.

'PINK ELF' is a hybrid that resulted from open-pollination of *Epimedium leptorrhizum* and presumably *Epimedium pubescens*. The seed parent is an individual *Epimedium leptorrhizum* (unpatented). The exact pollen parent is unknown but is presumed to be an individual *Epimedium pubescens* (unpatented).

The open-pollination occurred in 1992 at the inventor's nursery in Hampshire, England. 'PINK ELF' is readily distinguishable from the seed parent and the presumed pollen parent, by flower shape and flower color. The inventor selected 'PINK ELF' in 1992 based on the distinguishing characteristics of flower shape and flower color. There are no close comparison plants known to the inventor.

'PINK ELF' is semi-evergreen, characterized by clumping habit, heart-shaped leaflets that are green and russet in color, and purple-pink spurred flowers that are held above the leaves. 'PINK ELF' exhibits two distinct layers of foliage due to the difference in length between basal stems and the subsequently basally branching stems. Essentially herbaceous, 'PINK ELF' will retain leaves when winter temperatures are above minus 10° C. Centigrade.

The first asexual reproduction of 'PINK ELF' was conducted in 1993 by the method of division. Division of 'PINK ELF' was accomplished by the inventor, at the inventor's nursery in Hampshire, England. Since that time the distinguishing characteristics of 'PINK ELF' have been determined stable, fixed and reproduce true to type in successive generations.

SUMMARY OF THE INVENTION

The following traits have been repeatedly observed and represent the characteristics of 'PINK ELF'. These traits in combination distinguish 'PINK ELF' from all other commercial varieties of *Epimedium* known to the inventor. 'PINK ELF' has not been tested under all possible conditions and phenotypic differences may be observed with variations in environmental, climatic and cultural conditions, without however, any variance in genotype.

1. 'PINK ELF' exhibits clumping habit.
2. The foliage of 'PINK ELF' is semi-evergreen.
3. 'PINK ELF' exhibits purple-pink spurred flowers that are held above two distinct layers of foliage.
4. 'PINK ELF' exhibits heart-shaped leaflets that are russet in color when juvenile, and which change to green as the season advances.
5. 'PINK ELF' is propagated by the method of division.
6. At maturity 'PINK ELF' ranges from 60 cm. to 90 cm. in width, and ranges from 25 cm. to 40 cm. in height when in bloom.
7. Cultural requirements of 'PINK ELF' are full deep shade to partial shade, fertile humus-rich soil, and regular water.
8. 'PINK ELF' is hardy to minus 10° Centigrade and will retain leaves above this temperature.
9. 'PINK ELF' is suitable for use in container, rock garden, or as a groundcover for the landscape.
10. 'PINK ELF' blooms in March, April, May and sporadically again in September and October.

BRIEF DESCRIPTION OF THE DRAWINGS

The accompanying color drawings

Figure 1:
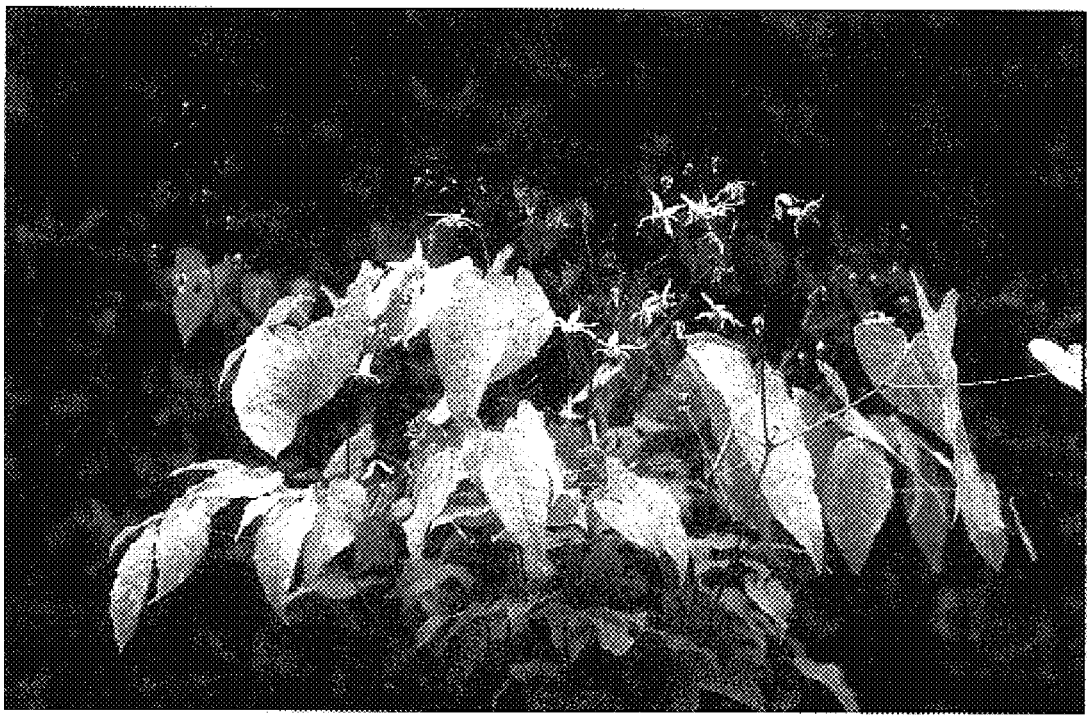
FIG. 1, FIG. 2, FIG. 3 and FIG. 4 illustrate the overall appearance of the new

*Epimedium* cultivar 'PINK ELF' showing the colors as true as it is reasonably possible to obtain in colored reproductions of this type. The drawings were made in May and June 2005 from 12-month-old plants in 2-liter containers. The plants were greenhouse grown in Hampshire, England. Colors in the drawings may differ from the color values cited in the detailed botanical description, which accurately describe the actual colors of 'PINK ELF'.

The drawing labeled as FIG. 1 depicts a single whole plant of 'PINK ELF' in flower.

Figure 2:
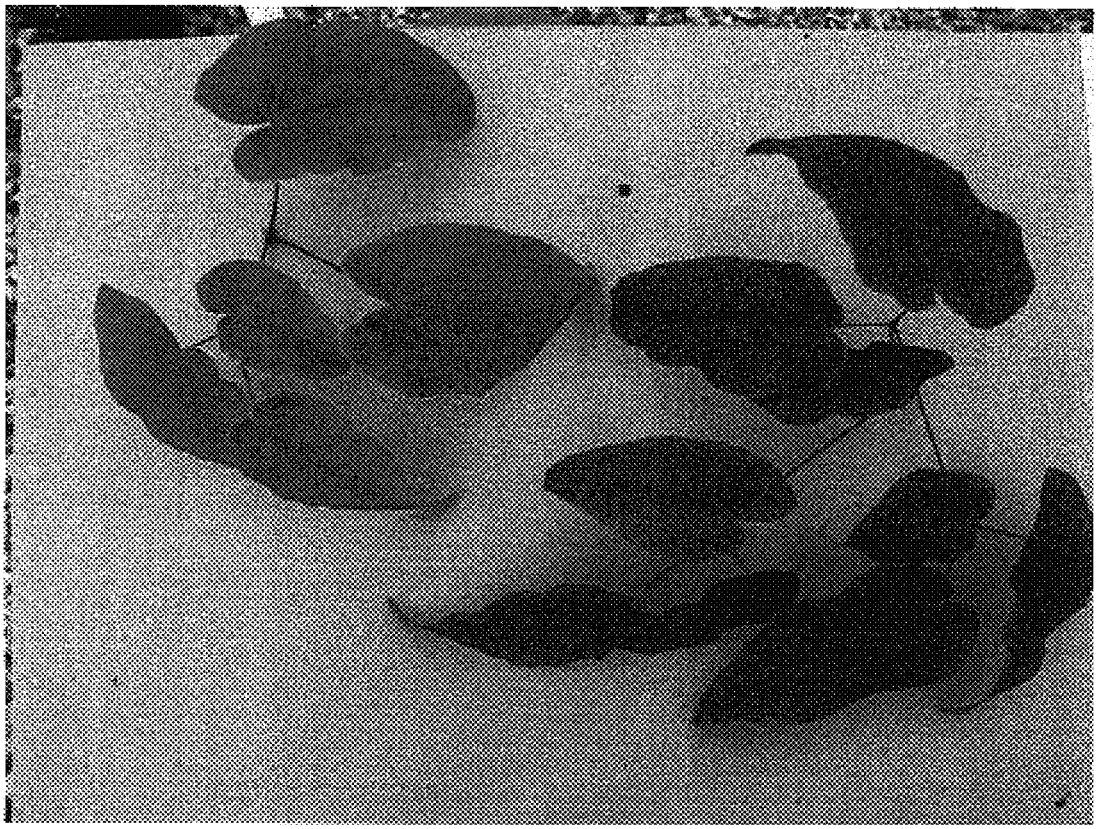

The drawing labeled as FIG. 2 depicts a close-up view of the mature foliage and illustrates the variability in leaflet arrangement which may include on the same individual plant either one or two or three sets of three leaflets, or simply individual leaflets, or a combination of single and set or sets of three leaflets.

Figure 3:
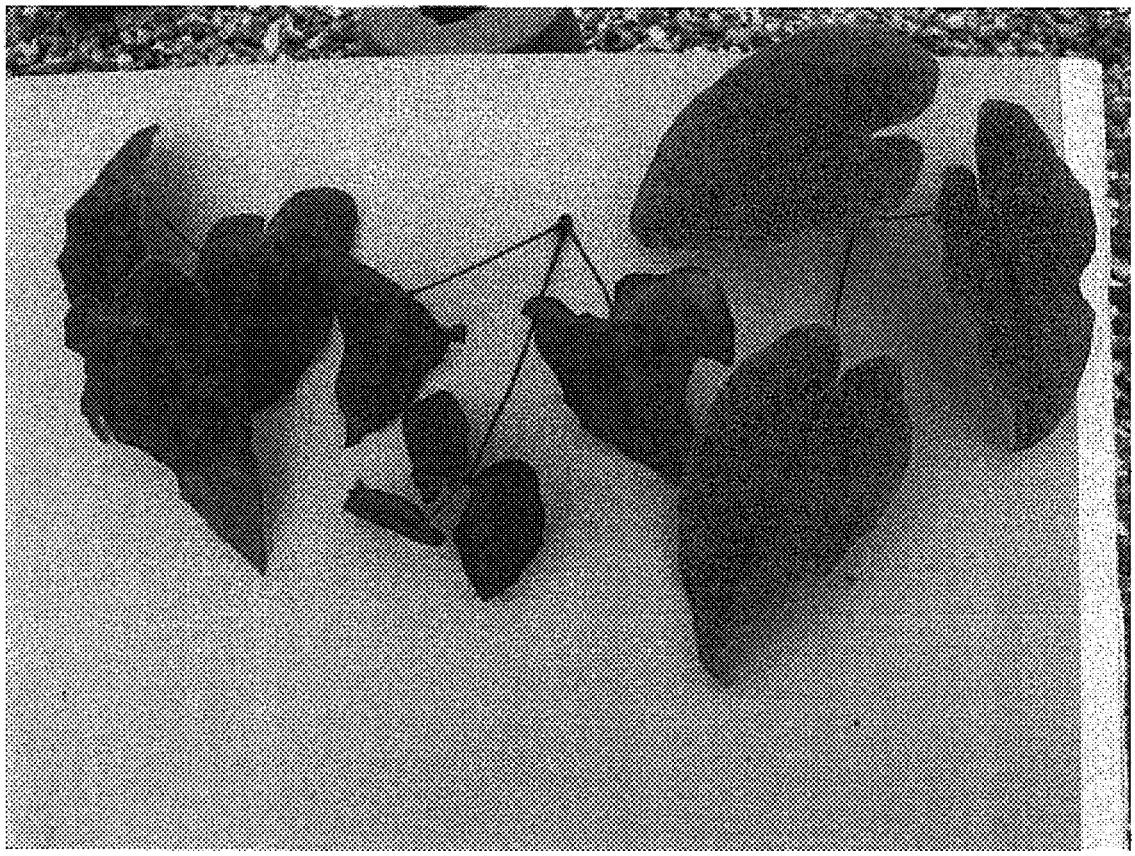

The drawing labeled as FIG. 3 depicts a close-up view of the mature and juvenile leaflets. The juvenile leaflets, shown on the left of the drawing, are initially reddish brown in coloration, which gradually changes to yellow-green as spring advances. The leaflets, when mature, are shown on the right of the drawing, and are uniformly green in color.

Figure 4:
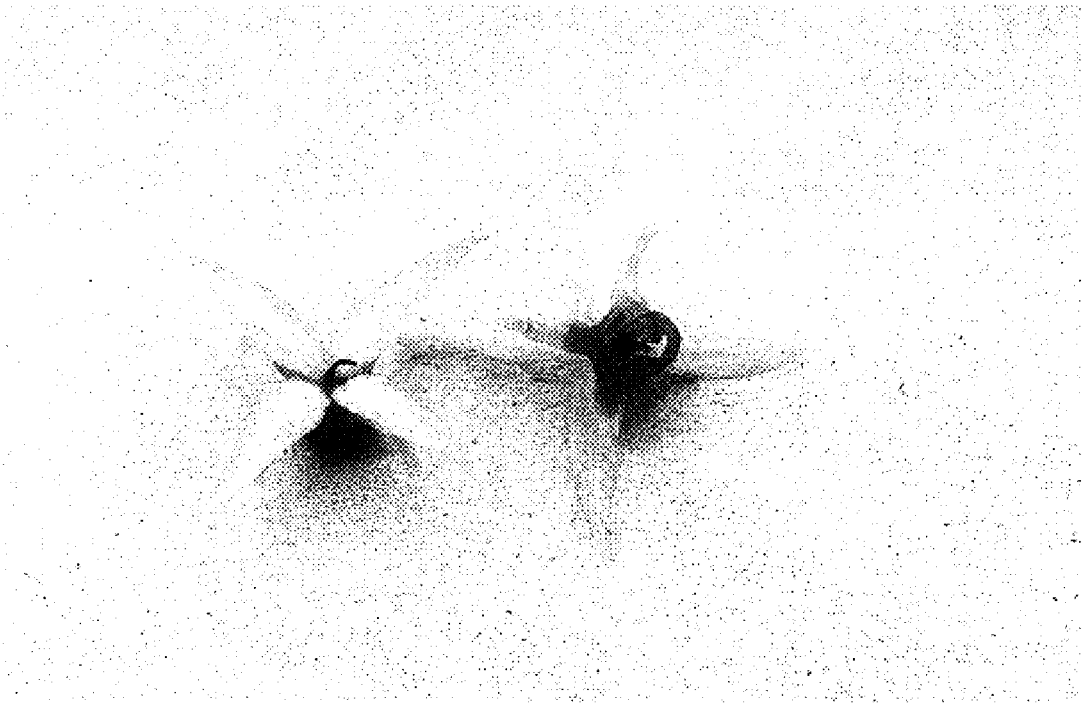

The drawing labeled as FIG. 4 depicts a close-up view of an inflorescence of 'PINK ELF' which is suspended from the peduncle. The ventral aspect of the flower is downward facing and is shown on the right of the drawing with the flower rotated through 180 degrees. The dorsal aspect of the flower is shown on the left of the drawing.

FIG. 1, FIG. 2, FIG. 3 and FIG. 4 were made using conventional techniques and although colors may appear different from actual colors due to light reflectance they are as accurate as possible by conventional photography.

BOTANICAL DESCRIPTION OF THE PLANT

The following is a detailed description of the new *Epimedium* variety named 'PINK ELF'. Data was collected from 2-liter container plants that were greenhouse grown in Hampshire, England. The color determinations are in accordance with the 2001 edition of The Royal Horticultural Society Colour Chart, except where general color terms of ordinary dictionary significance are used. The growing requirements are similar to the species.

Botanical classification: *Epimedium* sp. 'PINK ELF'.
Genus: *Epimedium.*
Species: sp.
Denomination: 'PINK ELF'.
Common name: Bishop's hat.
Commercial classification: Ornamental.
Plant type: Herbaceous perennial.
Commercial container size: Recommended commercial size is a 2-liter container.
Cultural requirements: Provide full deep shade to partial shade, fertile humus-rich soil, and adequate but not excess water.
Plant parentage: 'PINK ELF' is a hybrid that resulted from open-pollination of the following parent plants:
- *Seed parent.*—An individual *Epimedium leptorrhizum* (unpatented).
- *Pollen parent.*—The exact pollen parent is unknown but is presumed to be an individual *Epimedium pubescens* (unpatented).

Plant description:
- *Blooming period.*—March, April, May and sporadically in September and October.
- *Plant habit.*—Clumping habit.
- *Plant use.*—Grown for use in container, rock garden or as a groundcover for the landscape.
- *Vigor.*—Vigorous.
- *Root system.*—Fine and fibrous roots.
- *Plant width* (*at maturity*).—At maturity 'PINK ELF' ranges from 60 cm. to 90 cm. in width.
- *Plant height* (*at maturity*).—In bloom at maturity 'PINK ELF' ranges from 25 cm. to 40 cm. in height.
- *Plant growth rate.*—Plant spreads by rhizomes 1.5 cm. to 2.5 cm. annually.
- *Plant hardiness.*—Hardy to minus 10° Centigrade.
- *Plant propagation.*—Propagation is accomplished using the method of division.
- *Crop time.*—12 months are needed to produce a commercial 2-liter container plant from division.
- *Special growing considerations.*—Cut back in late winter before new growth resumes, and divide clumps in spring.
- *Pest and disease resistance and susceptibility.*—No particular susceptibility or resistance to pests or diseases have been noted to date. In general, *Epimediums* are considered resistant to eating or browsing by deer but such has not yet been determined or confirmed for 'PINK ELF'.

Stem:
- *Branching habit.*—Basal stems arise from rhizomes with some branching at or around aerial emergence. All stems appear to arise from the base. The basally branching stems bear foliage at a height of 6 cm to 8 cm above the foliage of the basal (rhizomatous) stems.
- *Stem color.*—152A.
- *Stem dimensions.*—Ranges from 1 mm. to 3 mm. in diameter and ranges from 6 cm. to 26 cm. in length.
- *Stem surface.*—Glaucous.
- *Stem shape.*—Cylindrical.
- *Stem texture.*—Wiry.
- *Stem strength.*—Moderate.
- *Stem pubescence.*—None observed.
- *Rhizome color.*—Colors 185A, 185B, and 186D are individually present on an individual rhizome.
- Rhizome diameter: 2 mm. to 2.5 mm. in diameter.
- *Rhizome internode.*—Internode is 2 cm. in length.

Foliage:
- *Foliage type.*—Semi-evergreen.
- *Leaf arrangement.*—Whorled: number of leaflets on both the basal and the cauline stem varies on an individual plant from one set of three leaflets to two or three sets of three leaflets. Alternatively, an individual plant may carry two sets of three leaflets and one single leaflet. Yet another possible arrangement is simply three single leaflets.
- *Leaf division.*—Biternate compound leaf.
- *Basal and cauline leaflet texture* (*juvenile leaflets*).—Satiny texture.
- *Basal and cauline leaflet texture* (*mature leaflets*).—Leathery texture.
- *Durability of basal and cauline leaflets to stress.*—Moderate to high durability.
- *Basal and cauline leaflet margins* (*juvenile and mature*).—Denticulate margins.
- *Basal and cauline leaflet shape* (*juvenile and mature*).—Lanceolate in shape.
- *Basal and cauline leaflet apex* (*juvenile and mature*).—Acuminate apex.

*Basal and cauline leaflet base* (*juvenile and mature*).—Cordate base.
*Basal and cauline juvenile leaflet pubescence* (*abaxial and adaxial surfaces*).—None observed.
*Basal and cauline mature leaflet pubescence* (*abaxial and adaxial surfaces*).—None observed.
*Basal and cauline juvenile leaflet surface* (*abaxial surface*).—Glossy surface.
*Basal and cauline juvenile leaflet surface* (*adaxial surface*).—Matte surface.
*Basal and cauline mature leaflet surface* (*abaxial surface*).—Glossy surface.
*Basal and cauline mature leaflet surface* (*adaxial surface*).—Matte surface.
*Basal and cauline juvenile leaflet length.*—Juvenile leaflet is 3.5 cm. in length.
*Basal and cauline mature leaflet length.*—Mature leaflet is 10 cm. in length.
*Basal and cauline juvenile width.*—Juvenile leaflet is 2 cm. in width.
*Basal and cauline mature leaflet width.*—Mature leaflet is 6 cm. in width.
*Basal and cauline leaf and leaflet attachment.*—Petiolate attachment.
*Basal petiole dimensions.*—6 cm. in length and 2.50 mm. in diameter.
*Cauline petiole dimensions.*—6 cm. in length and 2.50 mm. in diameter.
*Basal and cauline petiole color.*—A combination of colors 199A and 166B on an individual petiole.
*Basal petiolule dimensions* (*juvenile and mature*).—Petiolule is 1.50 mm. in diameter and ranges from 3 cm. to 5 cm. in length.
*Cauline petiolule dimensions* (*juvenile and mature*).—Petiolule is 1.50 mm. in diameter and ranges from 3 cm. to 5 cm. in length.
*Basal and cauline petiolule color* (*juvenile and mature leaves*).—A combination of colors 199A and 166B on an individual petiolule.
*Basal and cauline juvenile leaflet color* (*abaxial surface*).—Individual colors 166A, 166B, and 146B are present on an individual leaflet.
*Basal and cauline juvenile leaflet color* (*adaxial surface*).—Individual colors 166A, 166B, and 146B are present on an individual leaflet.
*Basal and cauline mature leaflet color* (*abaxial surface*).—146B.
*Basal and cauline mature leaflet color* (*adaxial surface*).—147C.
*Basal and cauline venation pattern* (*juvenile and mature leaflets*).—Palmate.
*Basal and cauline juvenile leaflet vein color* (*abaxial surface*).—146A.
*Basal and cauline juvenile leaflet vein color* (*adaxial surface*).—166A.
*Basal and cauline mature leaflet vein color* (*abaxial surface*).—146A.
*Basal and cauline mature leaflet vein color* (*adaxial surface*).—138A.
*Fragrance.*—None observed.

Flower:
*Inflorescence type.*—Compound panicle.
*Number of flowers and buds.*—22–50 flowers and buds combined per individual 2-liter container plant.
*Bloom period.*—March, April, May and sporadically in September and October.
*Flower shape.*—Like a bishop's hat in shape.
*Flower diameter* (*sepal tip to sepal tip*).—Individual flowers range from 1.8 cm. to 2 cm. in diameter.
*Flower diameter* (*spur tip to spur tip*).—Flowers range from 1.3 cm. to 1.5 cm. in diameter.
*Flower depth.*—Individual flowers are 1.75 cm. in depth.
*Flower color.*—Individual colors 179B, 179C, 161A, and 186D are present on an individual flower.
*Flower petal.*—Four petals in number.
*Petals fused or unfused.*—Petals are fused.
*Petal color* (*ventral and dorsal surfaces*).—A combination of colors 179B and 179C on an individual petal.
*Petal dimensions* (*length*).—9 mm to 10 mm.
*Petal dimensions* (*width, depth, at base*).—Width 4 mm, depth 3 mm.
*Petal dimensions* (*width, depth, at 5 mm from base*).—Width 1.5 mm, depth 1.5 mm.
*Calcar* (*spur*).—Four in number.
*Calcar color.*—161A.
*Calcar dimensions.*—2 mm. in diameter and 1 cm. in length.
*Bud shape.*—Globular in shape.
*Bud surface.*—Pubescent.
*Bud apex.*—Obtuse apex.
*Bud color.*—187B.
*Bud dimensions.*—4 mm. in diameter and 4 mm. in height.
*Sepals.*—8 sepals in number per individual flower, 4 dorsal sepals and 4 ventral sepals. The 4 dorsal sepals are shed as an individual flower opens.
*Dorsal sepal surface* (*abaxial surface*).—Pubescent.
*Dorsal sepal surface* (*adaxial surface*).—Pubsecent.
*Ventral sepal surface* (*abaxial surface*).—Pubescent.
*Ventral sepal surface* (*adaxial surface*).—Pubescent.
*Dorsal sepal shape.*—Broadly ovate in shape.
*Ventral sepal shape.*—Narrowly lanceolate in shape.
*Dorsal sepal color.*—187B.
*Ventral sepal color.*—186D.
*Sepal margin* (*dorsal and ventral sepals*).—Entire.
*Sepal apex* (*dorsal sepal*).—Acuminate.
*Sepal apex* (*ventral sepal*).—Reflexed acuminate apex.
*Dorsal sepal length.*—Dorsal sepal ranges from 2 mm. to 2.5 mm. in length.
*Dorsal sepal width.*—1.5 mm. in width.
*Ventral sepal length.*—Ventral sepal ranges from 1 cm. to 1.1 cm. in length.
*Ventral sepal width.*—Ventral sepal ranges from 2 mm. to 2.5 mm. in width.
*Peduncle dimensions.*—Individual peduncle is 14 cm. in length and 2 mm. in diameter.
*Peduncle surface.*—Glaucous surface.
*Peduncle color.*—197B.
*Pedicel dimensions.*—Individual pedicel is 1.25 mm. in diameter and ranges from 1.4 cm. to 2 cm. in length.
*Pedicel surface.*—Glaucous surface.
*Pedicel color.*—197B.
*Flower fragrance.*—None observed.

Reproductive organs:
*Stamens.*—4 stamens in number.
*Stamen color.*—152B.
*Pistil.*—One pistil in number.
*Pistil color.*—152B.
*Anther color.*—152B.
*Pollen color.*—152B.

Fruit:

*Fruit shape.*—Capsular.

*Fruit dimensions.*—1 cm. in length and 1 mm. in width.

*Fruit colors.*—Individual colors 146B and 165A are present on an individual fruit.

It is claimed:

1. A new and distinct cultivar of *Epimedium* plant named 'PINK ELF', as described and illustrated herein.

* * * * *